(12) United States Patent
Tullous

(10) Patent No.: US 8,074,312 B2
(45) Date of Patent: *Dec. 13, 2011

(54) MATTRESS INCORPORATING A HEADREST FOR PREVENTING AND CORRECTING NON-SYNOSTOTIC CRANIAL DEFORMITIES IN INFANTS

(76) Inventor: Micam W. Tullous, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/628,256

(22) Filed: Dec. 1, 2009

(65) Prior Publication Data

US 2010/0071138 A1   Mar. 25, 2010

Related U.S. Application Data

(63) Continuation of application No. 11/684,604, filed on Mar. 10, 2007, now Pat. No. 7,647,660, which is a continuation-in-part of application No. 11/449,402, filed on Jun. 8, 2006.

(51) Int. Cl.
*A61F 5/00* (2006.01)
*A47D 7/01* (2006.01)

(52) U.S. Cl. ............ 5/655; 5/731; 5/733; 5/632; 602/17; 128/845

(58) Field of Classification Search .............. 5/731–734, 5/740, 655; 128/845; 602/17, 18
See application file for complete search history.

(56) References Cited

U.S. PATENT DOCUMENTS

| | | |
|---|---|---|
| 2,876,459 A | 3/1959 | Ackerson |
| 3,877,093 A | 4/1975 | Gershbein |
| 4,383,713 A | 5/1983 | Roston |
| 4,631,766 A | 12/1986 | Semmler |
| 4,776,324 A | 10/1988 | Owen |
| 4,825,487 A | 5/1989 | Eberl |
| 5,048,136 A | 9/1991 | Popitz |
| 5,360,017 A | 11/1994 | Austin |
| 5,423,099 A | 6/1995 | Gulli |
| 5,524,640 A | 6/1996 | Lisak |
| 5,566,413 A | 10/1996 | Webb |
| 5,709,649 A | 1/1998 | Chitwood |
| 5,743,271 A | 4/1998 | Royo-Salvador |
| 5,820,573 A | 10/1998 | Ramos |

(Continued)

FOREIGN PATENT DOCUMENTS

| | | |
|---|---|---|
| DE | 20 2005 019 550 U1 | 4/2007 |
| EP | 0 880 925 A1 | 12/1998 |
| EP | 1 557 117 A1 | 7/2005 |

(Continued)

*Primary Examiner* — Michael Trettel
(74) *Attorney, Agent, or Firm* — John C. Cave; Gunn, Lee & Cave

(57) ABSTRACT

A device for correcting the shape of an infant's abnormally-shaped cranium by applying external forces over time with the growth of an infant to achieve normal shaping of the infant's head. The device applies inwardly-directed external forces only to areas of bony prominence and minimizes (or altogether eliminates) these forces on the areas of the skull that are less prominent (or flattened). Because the present invention is non-conforming to the shape of an abnormal skull, the exerted forces cause accelerated expansion of the skull in less prominent (flattened) areas coincident with brain and skull growth. This causes the cranium to return to a normal symmetric cranial shape. The material that contacts the infant's cranium is semi-rigid, relatively non-flexible, and maintains its overall shape under stress. For an infant with an already normally-shaped cranium, the device causes the infant's cranium to grow evenly and maintain its normal shape, and thus prevents abnormal cranial shaping.

52 Claims, 9 Drawing Sheets

| U.S. PATENT DOCUMENTS | | | |
|---|---|---|---|
| 6,052,849 A | 4/2000 | Dixon | |
| 6,088,855 A | 7/2000 | Connolly | |
| 6,321,403 B1 | 11/2001 | Matthews | |
| 6,473,923 B1 | 11/2002 | Straub | |
| 6,536,058 B1 | 3/2003 | Chang | |
| 6,592,536 B1 | 7/2003 | Argenta | |
| 7,234,181 B1 | 6/2007 | Griggs | |
| 7,418,752 B2 | 9/2008 | Kemm | |
| 7,647,660 B2 * | 1/2010 | Tullous | 5/655 |
| 7,810,501 B2 * | 10/2010 | Rogers et al. | 128/845 |
| 2002/0174488 A1 | 11/2002 | Appleton | |

| FOREIGN PATENT DOCUMENTS | | |
|---|---|---|
| EP | 1 202 654 B1 | 11/2005 |
| EP | 1 864 595 A1 | 7/2007 |
| EP | 1 665 958 A1 | 12/2007 |
| ES | 2 241 617 | 8/2002 |
| FR | 2 859 615 | 3/2005 |
| GB | 2 412 062 A | 9/2005 |
| NZ | 51042 A | 1/2004 |
| WO | 2005/025385 A1 | 3/2003 |
| WO | 2005/092154 A1 | 10/2005 |
| WO | 01/00064 A1 | 1/2007 |

* cited by examiner

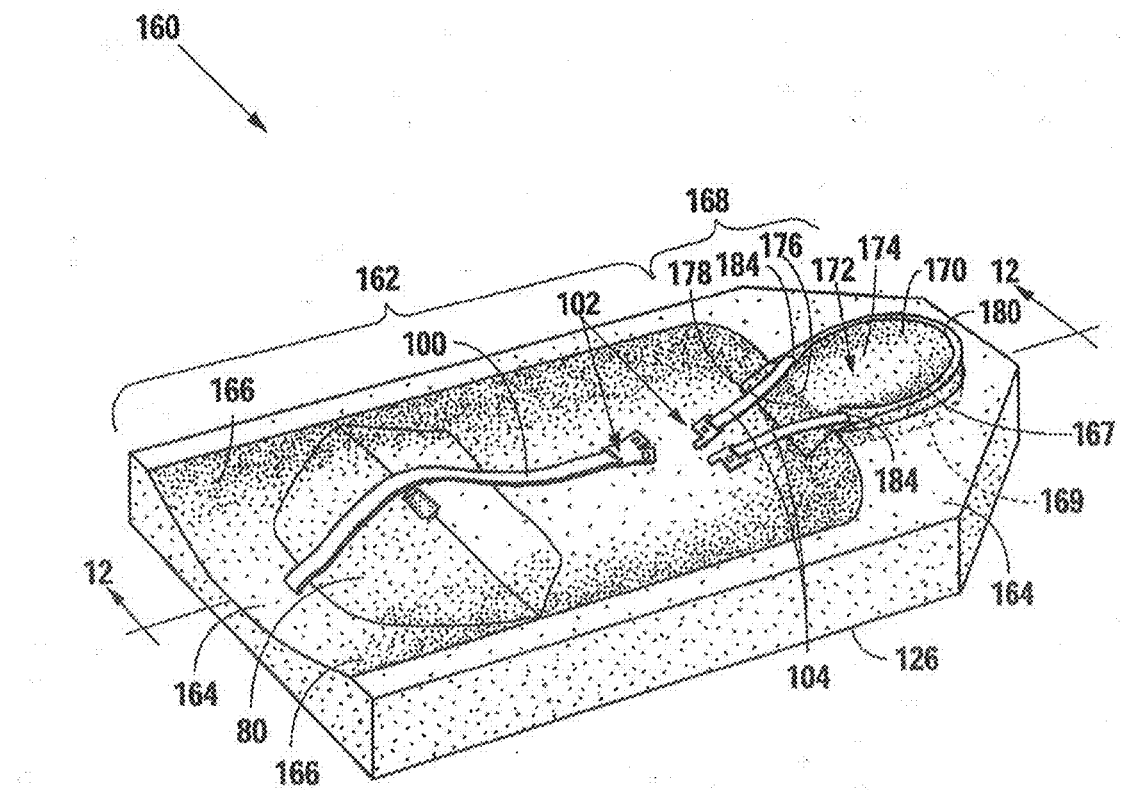

MATTRESS INCORPORATING A HEADREST FOR PREVENTING AND CORRECTING NON-SYNOSTOTIC CRANIAL DEFORMITIES IN INFANTS

CROSS REFERENCES TO RELATED APPLICATIONS

This is a continuation application claiming priority to U.S. patent application Ser. No. 11/684,604 filed Mar. 10, 2007, which is a continuation-in-part application claiming priority to U.S. patent application Ser. No. 11/449,402 filed Jun. 8, 2006. Each of these applications is incorporated herein by reference.

BACKGROUND OF THE INVENTION

1. Field of the Invention

The present invention relates generally to a mattress incorporating a headrest in which an infant's cranium is positioned while the infant is sleeping to prevent and correct cranial deformities. More specifically, the invention relates to a mattress incorporating a headrest for preventing and correcting any non-synostotic deformity of the side and posterior aspects of an infant's head.

2. Description of Related Art

At birth, the six cranial bones comprising an infant's skull are spaced far enough apart to allow the skull to rapidly grow during the first months of the infant's life. This spacing also allows the bones to overlap so the infant's head can pass through the birth canal without compressing, and thereby damaging, the infant's brain. Eventually—some time between three and six years of age—the cranial bones will fuse and remain fused for the rest of the child's life. During an infant's normal growth, forces within the infant's skull are directed outward and are constant and equally distributed on the inner surface of the growing skull causing the skull to expand. Accordingly, a decrease of the intracranial pressure will cause a reduced head size. Similarly, an increase in intracranial pressure will cause an increased head size.

Fibrous bands of tissue, called cranial sutures, fill the space between the bones and connect the bones of the skull to each other. These cranial sutures are strong and elastic, providing a flexibility to the skull to allow rapid brain growth during the first months of life. Without the sutures, a child would suffer brain damage due to constriction of the brain during the period of normal growth.

During the first few months of an infants' life, however, the infant is most susceptible to the formation of synostotic or non-synostotic deformities in the cranium. Synostotic deformities are a result of craniosynostosis, which is a birth defect of the skull characterized by premature closure of one or more of the cranial sutures. Craniosynostosis can be hereditary or the result of a metabolic disease, and is characterized by an abnormally-shaped skull and potential for abnormal intracranial pressure, mental retardation, seizures, and blindness.

On the other hand, non-synostotic deformities, in which the cranial sutures remain open, are caused by environmental conditions, including premature birth, torticollis (twisting of the neck muscles beyond their normal position), or the preferred sleeping position of the child. In addition, neurological abnormalities, such as paralysis, cerebral palsy, or some sort of developmental delay, may predispose a child to cranial positioning problems. Non-synostotic deformities are also called positional deformities.

Synostotic and non-synostotic deformities manifest themselves in a variety of ways. Plagiocephaly, for example, is a cranial deformity resulting in an asymmetric head shape. Plagiocephaly consists of a focal area of flattening in the anterior or posterior aspect of one side of the head, which also commonly produces additional compensatory deformities in adjacent areas of the skull, skull base, and face, including the orbital (eye) and mandibular (jaw) structures. This deformity most commonly occurs in the posterior aspect of the head (posterior plagiocephaly), resulting in a focal area of flattening on that side and a compensatory prominence, or bulge, on the other side. In addition, the deformity produces anterior displacement of the ear, ear canal, temporomandibular (jaw) joint, forehead and orbital structures on the same side. Cranial deformities may also be classified, inter alia, as brachycephaly (a short, wide head shape), scaphocephaly (a long, narrow head shape), and turricephaly (a pointed head shape).

Non-synostotic posterior plagiocephaly is a very common problem for which parents seek evaluation and recommendations from their family physician or pediatrician. The incidence of this abnormality has increased significantly since publication of recommendations by the American Academy of Pediatrics that neonates (infants) should be put to sleep on their back rather than face down. These recommendations were made to reduce the incidence of Sudden Infant Death Syndrome (SIDS) by eliminating airway and respiratory compromise in the prone (face-down) position, which the Academy considered a possible contributor to the SIDS problem.

The usual method of attempting to treat these deformities involves trying to reposition the child during sleep. The most common adjuncts available to assist with this treatment are flat- and wedge-shaped foam pads. For example, U.S. Pat. No. 6,473,923 (filed Nov. 22, 2000) (issued Nov. 5, 2002) discloses a body pillow and head positioner attached to a mat. The device is intended to maintain the infant's supine position while reducing the risk of positional plagiocephaly by causing the head to rotate to the side while maintaining the infant's supine position.

Simply put, repositioning, even with foam padding, is ineffective for treating or preventing these deformities, and even after treatment most children do not obtain a perfectly normal head shape. Repositioning merely distributes or disperses the forces over a larger area of the head. The foam padding remains in contact with the skin and conforms the head to an abnormal shape. Due to this ineffectiveness, a large number of these children require additional treatment from five to ten months of age due to persistent or progressive deformities.

The additional treatment most often is by application of a custom-made external orthosis, or helmet. See, e.g., Corrective Infant Helmet, U.S. Pat. No. 6,592,536 (filed Jan. 7, 2000) (issued Jul. 15, 2003); Therapeutic and Protective Infant Helmets, U.S. Pat. No. 4,776,324 (filed Apr. 17, 1998) (issued Oct. 11, 1998). Such devices provide an expanded area over the site of the deformity, thereby allowing for correction of the deformity over a three- to six-month period of time related to brain and skull growth and subsequent reshaping. This prolonged time of use is necessary because of the reduced rate of brain and skull growth during the six- to twelve-month time frame. Due to a decrease in the rate of brain and skull growth to approximate fifty percent of the rate from birth to six months and increased stiffness of bones and cranial sutures, the recommendation is to wear the helmet continuously for twenty-three hours each day for up to twelve months. But despite extended use of these helmets, deformities rarely return to a normal shape. In addition, many health insurance companies and programs refuse to pay for these devices, leaving a large number of infants with no available treatment because of the relatively high cost of the helmets.

Another approach to correcting cranial deformities is to soften the material on which the infant's head rests by using a foam pad or memory foam pillow. This method allows the redistribution of inwardly directed forces over a slightly larger surface area, but fails to adequately correct cranial deformities because the softened material conforms to the head shape. The material still contacts, and therefore applies forces to, flattened areas instead of only the abnormal cranial bulges. Preventing cranial deformities with this approach is also ineffective because forces continue to act directly on a focused area of the head. Forces acting on a smaller area of the head results in cranial flattening, and therefore an abnormal head shape, because the head conforms to the shape of the material at the point of contact.

Still another approach is to suspend the infant's head on a flexible material, which, for example, may be a net with an open weave that keeps the infant's head slightly elevated over the resting surface. See Method and Apparatus to Prevent Positional Plagiocephaly in Infants, U.S. Pat. No. 6,052,849 (filed Mar. 18, 1999) (issued Apr. 25, 2000). Although the use of an elastic stretchable material or netting may be slightly better than regular foam for preventing the development of flattened areas, these devices do not promote normal shaping due to the continuous application of external forces directed at a smaller posterior aspect of the infant's head. As with the "softened material" approach previously described, forces acting on a smaller area of the head results in cranial flattening because the head conforms to the shape of the stretched material, thus resulting in an abnormal head shape in which the frontal areas are wider than the posterior aspect of the head.

After ten to twelve months of age, little, if any, correction of a cranial deformity can be accomplished with non-operative treatment because of reduced velocity of brain and skull growth, increased thickness of bone, and reduced flexibility of the cranial sutures. Surgical intervention is typically the only effective treatment for moderate to severe deformities in children over twelve months of age.

The prior art for treating this condition does not directly address the cause of the problem, and therefore does not effectively treat the condition. All other products and devices, including foam, elastic (and therefore flexible) material or netting, merely distribute or disperse forces over a larger area of the head. Because these products and devices remain in contact with the skin, they therefore conform the cranium to the abnormal shape. Thus, the prior art does not remove or eliminate the external forces at flattened areas of the cranium, but rather maintains an abnormal cranial shape and promotes a static deformity.

Currently there is no specific apparatus available to provide effective corrective and preventative treatment for non-synostotic cranial deformities in the age range of birth to five months. To avoid the difficulties and pitfalls associated with currently available devices aimed at treating non-synostotic cranial deformities, the present invention discloses a corrective headrest for use at the very first recognition of development of a deformity. The headrest and method allow effective treatment during the rapid period of brain and skull growth (birth to six months), thereby providing rapid correction of the deformity. Children with predisposing conditions possibly require prolonged treatment. Early effective treatment is the key to providing complete correction of these deformities.

BRIEF SUMMARY OF THE INVENTION

The present invention discloses a mattress incorporating a headrest for correcting and preventing the shape of an infant's abnormally-shaped cranium by applying external forces over time with the growth of an infant to achieve normal shaping of the infant's head. Unlike the prior art, the present invention both 1) prevents abnormal shaping of an infant's cranium by causing even growth of the infant's normally shaped head and 2) provides forces that act unevenly across an abnormally shaped cranium to correct existing cranial deformities. The embodiments of the present invention include a mattress incorporating a headrest having a depression that approximates the posterior and side aspects of the skull and head, with cervical, or neck, support. The headrest can be formed as part of the mattress or as a separate piece that fits and is received into a cavity in the mattress. The headrest material that contacts the infant's cranium is semi-rigid and relatively nonflexible, maintains its overall shape under stress, and demonstrates minimal superficial focal elasticity only at the site of cutaneous contact.

The mattress is concave with raised sides and maintains the infant in a supine position. A raised leg rest supports the infant's knees and helps position the infant so that the infant's head rests within the depression in the headrest.

To correct existing cranial deformities, the headrest of the present invention applies inwardly-directed external forces only to areas of bony prominence and minimizes (or altogether eliminates) these forces on the areas of the skull that are less prominent (or flattened). The present invention is non-conforming to the shape of an abnormal skull. The forces exerted allow for accelerated expansion of the skull in the less prominent (flattened) areas coincident with brain and skull growth, allowing for return to a normal symmetric cranial shape.

The headrest prevents development of abnormal cranial shaping by providing a round, normally-shaped contour for the posterior and side aspects of the head, even if the head is turned slightly to one side or the other. Because the contour is normally shaped, substantially the entire surface area of the normally-shaped cranium that rests in the depression continuously contacts the surface of the headrest. Moreover, because the contacting surface is semi-rigid, the surface will allow for even cranial growth over this area of contact, thereby maintaining the infant's normal head shape.

The preferred embodiment of the headrest of the present invention is made from a self-skinning foam, which provides ease of cleaning as well as flame retardant properties. Other embodiments of the present invention are made from other foam variants and/or materials, including closed cell foam and closed cell foam layered over or applied to more rigid solid or hollow plastic (e.g., PVC or nylon). In addition, the present invention may be made from open cell foam to which has been applied a surface treatment, such as a vinyl or other coating, impregnating paint into the surface during the molding process, or painting the surface.

BRIEF DESCRIPTION OF THE SEVERAL VIEWS OF THE DRAWINGS

The present invention, as well as further objects and features thereof, are more clearly and fully set forth in the following description of the preferred embodiments, which should be read with reference to the accompanying drawings, wherein:

FIG. 11 discloses a perspective view of a third alternative embodiment of the present invention having a removable headrest;

FIG. 12 illustrates a sectional view of the third alternative embodiment along section line 12-12 of FIG. 11;

DETAILED DESCRIPTION OF THE PREFERRED EMBODIMENTS

Figure 1:
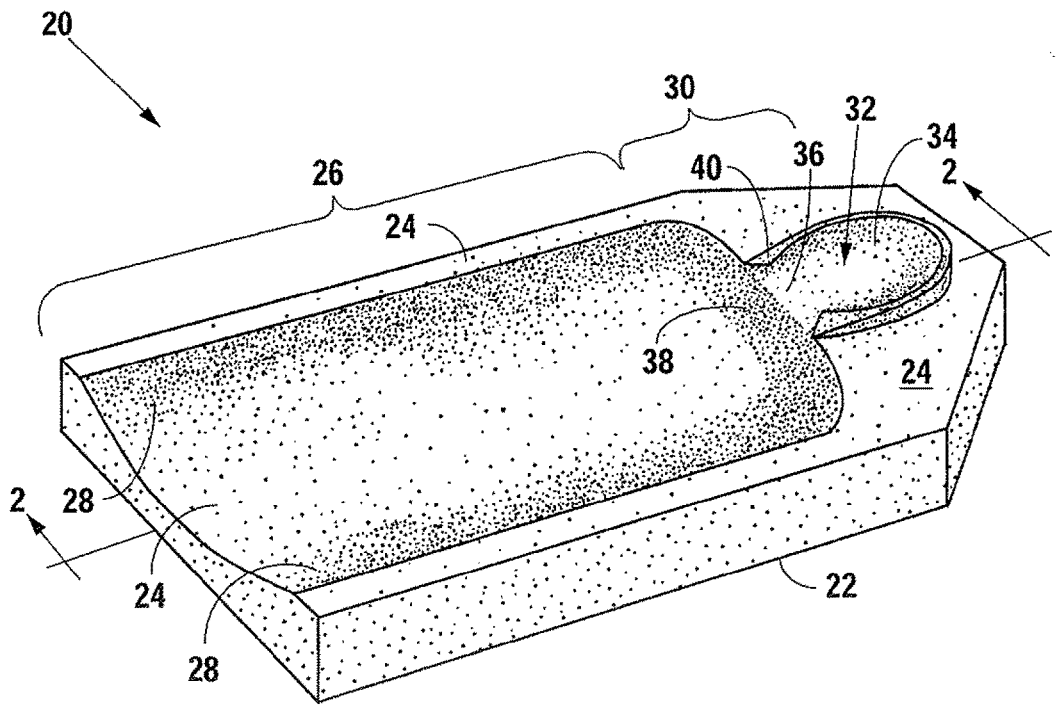
FIG. 1 shows a perspective view of the preferred embodiment of the present invention.
Figure 2:
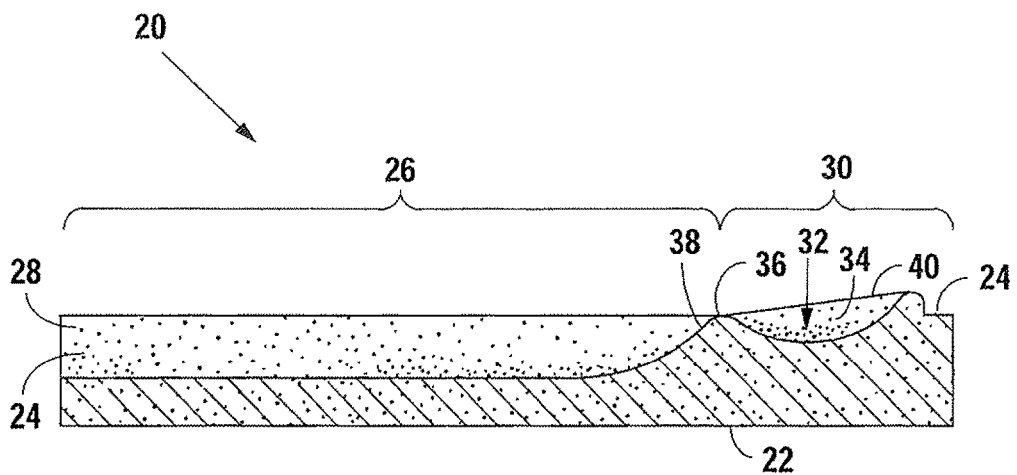
FIG. 2 illustrates a sectional view of the preferred embodiment along section line 2-2 of FIG. 1.
Figure 3:
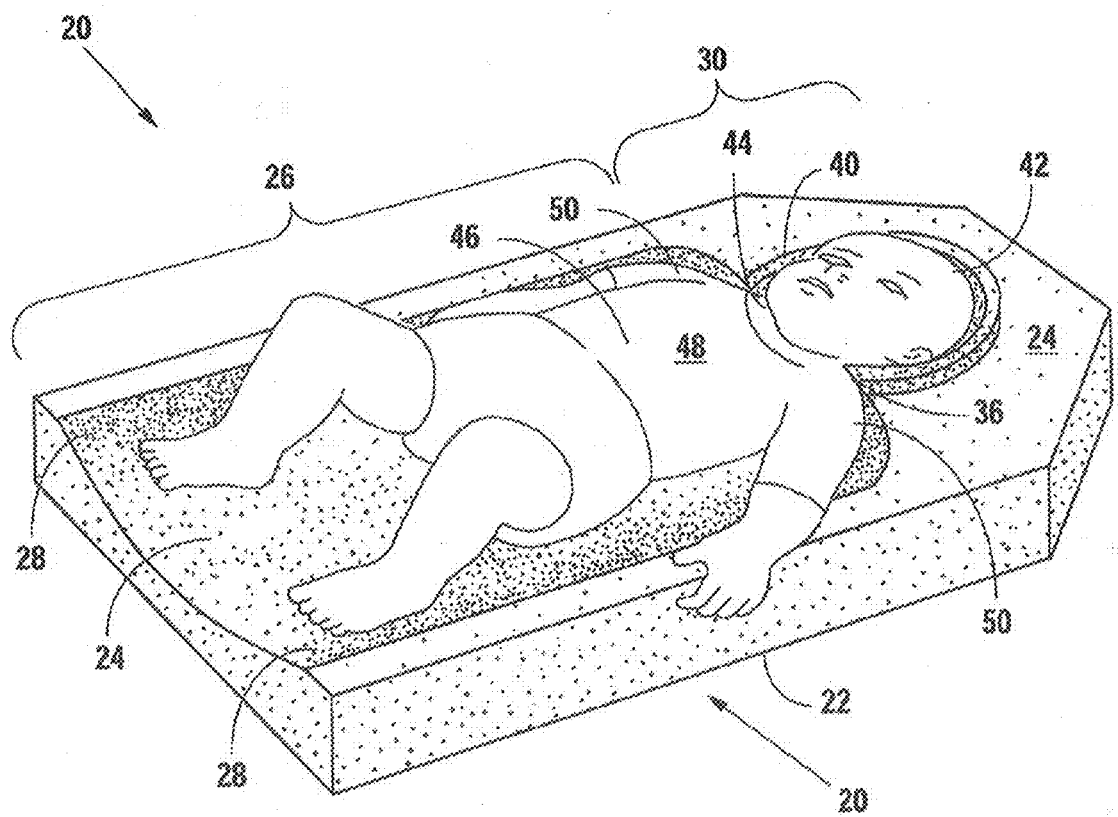
FIG. 3 shows a perspective view of an infant positioned in the preferred embodiment of the present invention.

FIGS. 1, 2 and 3 depict the preferred embodiment of present invention, which is a mattress incorporating a headrest for preventing and correcting non-synostotic cranial deformities in infants.

FIGS. 1 and 3 show a perspective view of the mattress 20. FIG. 2 illustrates a sectional view of the preferred embodiment along section line 2-2 of FIG. 1.

As shown in FIGS. 1, 2 and 3, the mattress 20 comprises a bottom surface 22 and a top surface 24. A body portion 26 of the top surface 24 of the mattress 20 is concave and has raised sides 28 to prevent an infant lying on the mattress 20 from rolling or moving from the infant's sleeping or resting position, as shown in FIG. 3. A headrest portion 30 of the mattress 20 further comprises a generally hemi-ellipsoidal depression 32 in the top surface 24 that corresponds to the shape of a normal infantile cranium. A semi-rigid surface 34 of the depression 32 is resilient, and preferably made of self-skinning foam. A ridge 36 is adjacent to one end of the depression 32, and a curved intermediate surface 38 positioned between the ridge 36 and the body portion 26 of the mattress 20. A rim 40 defines a substantial portion of the outer edge of the depression 32.

The mattress 20 is preferably a single body molded from a self-skinning foam material. Alternatively, the mattress 20 may be made from a number of foam variants, including closed cell foam layered over higher density foam or layered over a more rigid solid or hollow plastic. In addition, the mattress 20 may be made from open cell foam to which has been applied a surface treatment such as, for example, using a vinyl or other coating, impregnating paint into the surface during the molding process, or painting the surface.

FIG. 3 depicts the preferred embodiment of the present invention in normal operation for the correction of an abnormally shaped infant cranium 42. The mattress 20 is placed on a resting surface (not shown) so that the bottom surface 22 is in contact therewith. The infant's cranium 42 is placed in the depression 32 with the infant's cranium 42 resting on the semi-rigid surface 34 of the depression 32 and the infant's neck 44 being supported by the ridge 36. The infant's body 46 is positioned in the body portion 26 of the mattress 20, where the raised sides 28 aid in preventing the infant 48 from rolling or moving from a sleeping or resting position. Initially the posterior and part of the side aspects of the infant's cranium 42 contact the semi-rigid surface 34 in the depression 32, although during the sleep period the infant's cranium 42 may roll to one side or the other. Throughout the sleep period, the infant's neck 44 is supported by the ridge 36. The infant's shoulders 50 are aligned in and cradled by the curved intermediate surface 38.

As the infant's cranium 42 makes contact with the semi-rigid surface 34 in the depression 32, the semi-rigid surface 34 provides external forces acting on any abnormal bulges of the infant's cranium 42 and diminishes or eliminates external forces that act on abnormal depressions of the infant's cranium 42. This contact reduces the net outward forces from brain and skull growth at these bulges, and redirects the growth to areas of depression in the cranium 42 which are lightly touching or not in contact with the semi-rigid surface 34.

The mattress 20 works similarly to prevent cranial deformities. With the infant's cranium 42 placed in the depression 32, the semi-rigid surface 34 of the depression 32 matches the round, normally-shaped contour of the posterior and side aspects of the infant's cranium 42. Thus, the semi-rigid surface 34 substantially and continuously contacts the entire surface area of the cranium 42 within the depression 32. Forces from the semi-rigid surface 34 act on the area of the cranium 42 in contact with the semi-rigid surface 34. The resulting pressure causes the infant's cranium 42 to grow evenly and maintain its normal shape. In other words, the contour of the normally-shaped semi-rigid surface 34 allows for the development of normal cranial shaping regardless of the cranium's 42 resting position by preventing abnormal growth (i.e., cranial bulges and cranial depressions) in the area of contact with the semi-rigid surface 34. The pressure caused by the forces acting on the cranium from the semi-rigid surface 34 is preferably substantially isometric.

Figure 4:
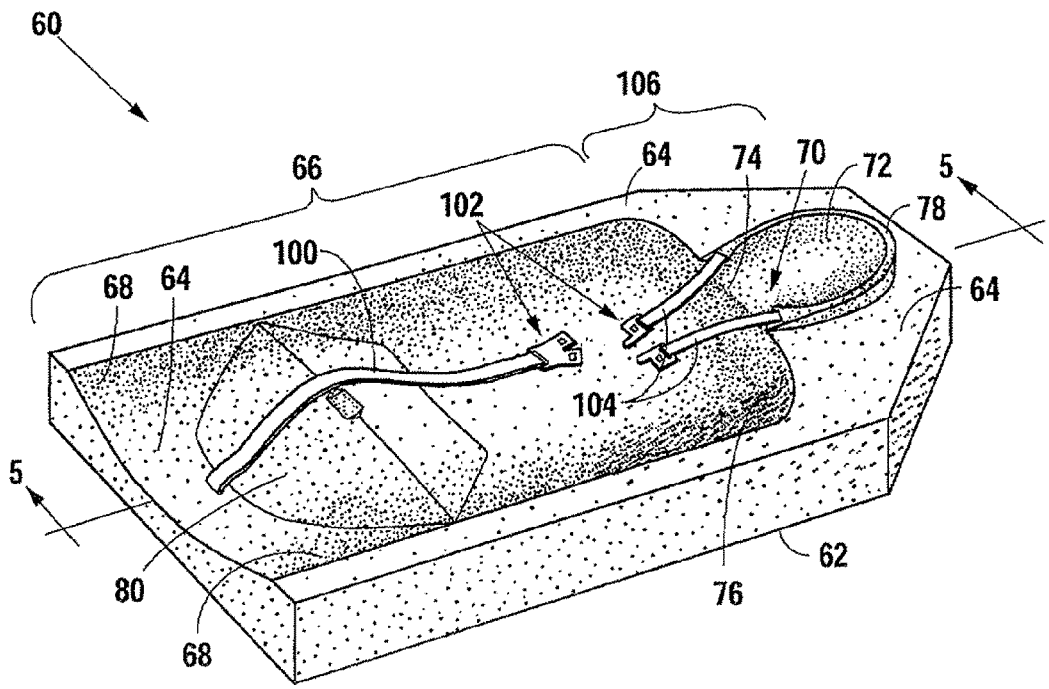
FIG. 4 is a perspective view of an alternative embodiment of the present invention that incorporates a harness and leg rest.
Figure 5:
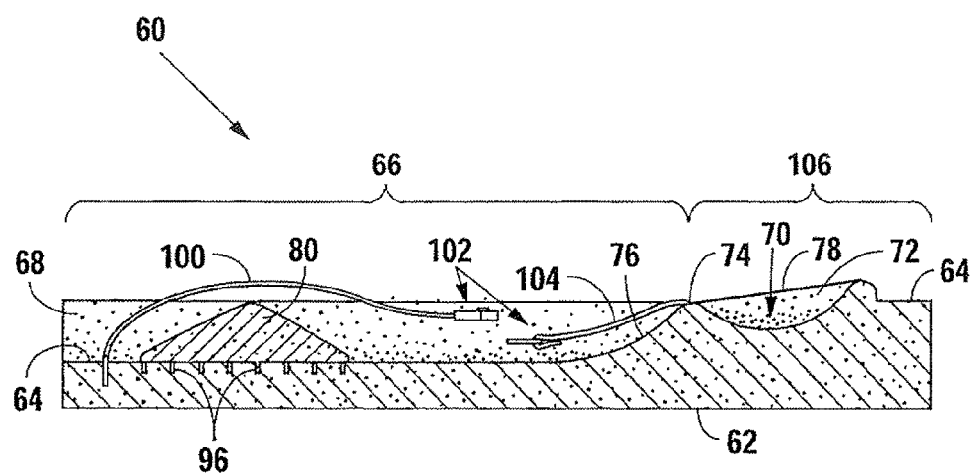
FIG. 5 illustrates a sectional view of the preferred embodiment along section line 5-5 of FIG. 4.
Figure 6A:
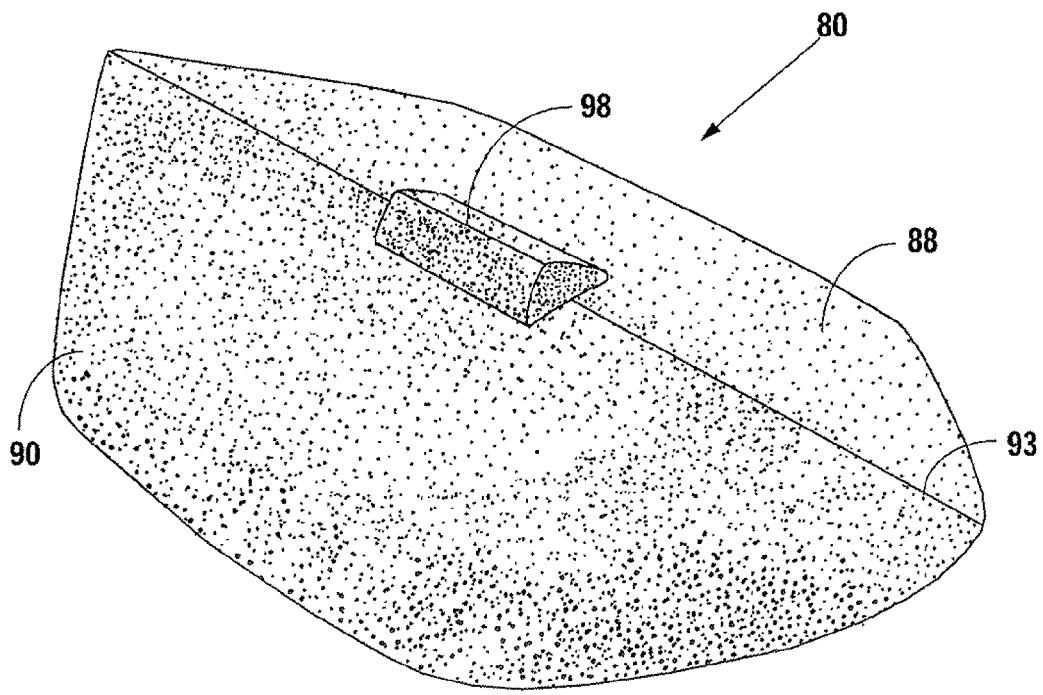
FIG. 6A and FIG. 6B depict the leg rest of the alternative embodiment.
Figure 6B:
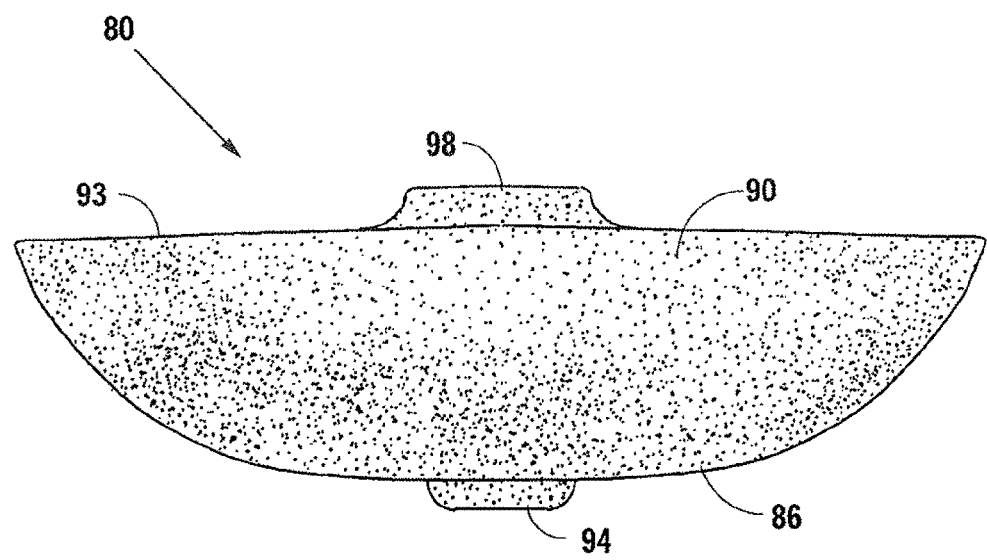
Figure 7:
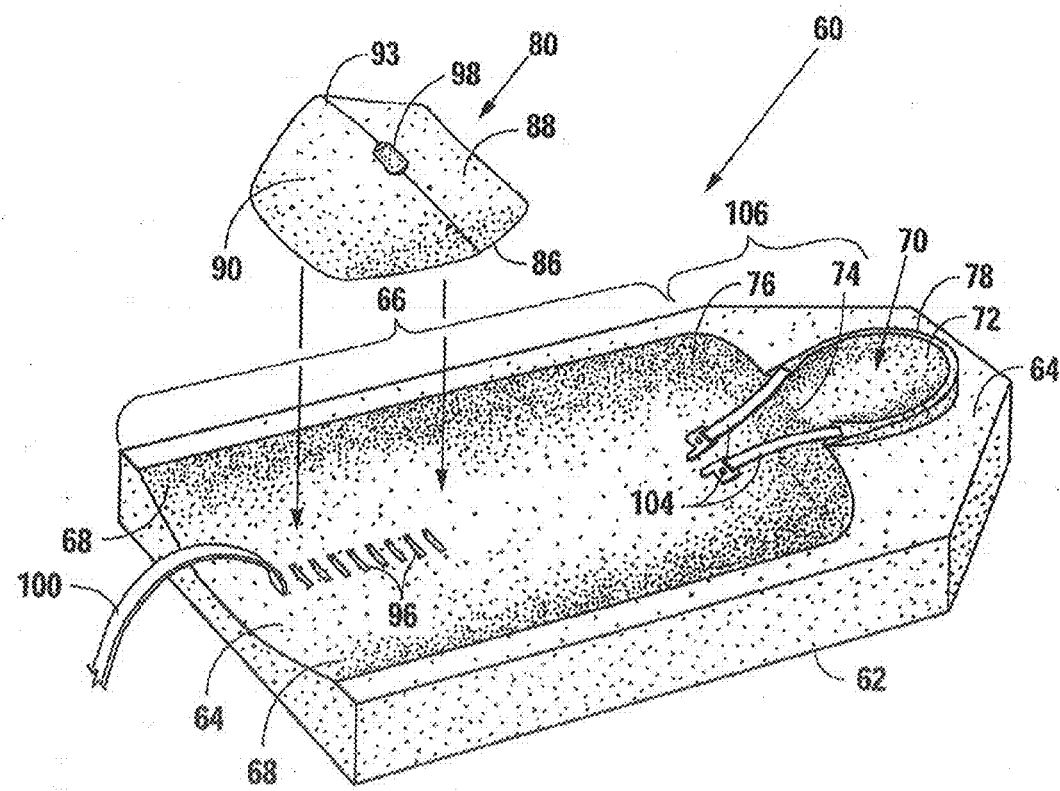
FIG. 7 illustrates an exploded view of the alternative embodiment of the present invention.

FIG. 4 through FIG. 8 depict a first alternative embodiment of the present invention. As shown in FIGS. 4, 5, and 7, the mattress 60 comprises a bottom surface 62 and a top surface 64. A body portion 66 of the top surface 64 of the mattress 60 is concave and has raised sides 68 to prevent an infant lying on the mattress 60 from rolling or moving from the infant's resting or sleeping position. The mattress 60 further comprises a generally hemi-ellipsoidal depression 70 in the top surface 64 that corresponds to the shape of a normal infantile cranium. A semi-rigid surface 72 of the depression 70 is resilient, and preferably made of self-skinning foam. A ridge 74 is adjacent to one end of the depression 70, and a curved intermediate surface 76 is positioned between the ridge 74 and concave body portion 66 of the mattress 60. A rim 78 defines a substantial portion of the outer edge of the depression 70.

The mattress 60 of this alternative embodiment includes a leg rest 80 for positioning an infant's legs thereon to increase the infant's comfort and to more effectively immobilize the infant during use, as will be described hereinafter. The leg rest 80 is preferably made from foam, although any material that comfortably supports the infant's legs may be used. Flame retardant materials and water-resistant materials may also be preferred over other materials.

As shown by FIG. 6A and FIG. 6B, the bottom surface 86 of the leg rest 80 conforms to the shape of the top surface 64 of the concave body portion 66 of the mattress 60 so that when the leg rest 80 is placed on the top surface 64, the bottom surface 86 of the leg rest 80 is flush with the top surface 64 of the body portion 66 of the mattress 60 (see FIGS. 4 & 5). The leg rest 80 further comprises a first side 88 and a second side 90 on which the infant's legs rest, the first side 88 supporting the legs 82 above the knees 92 and the second side 90 supporting the legs 82 below the knees 92 (see FIG. 8). The first side 88 and second side 90 meet at an apex 93 and are each adjacent to the bottom surface 86 of the leg rest 80.

A positioning tab 94 protrudes from the bottom surface 86 of the leg rest 80 and is preferably formed from the same material as the rest of the leg rest 80. As shown in FIG. 5 and FIG. 7, a plurality of positioning slots 96 are longitudinally aligned in the top surface 64 of the concave body 66 portion of the mattress 60 and positioned to receive the positioning tab 94. The positioning slots 96 are spaced to accommodate the leg position of infants of different lengths. By inserting the positioning tab 94 into one of the plurality of slots 96, the leg rest 80 may be longitudinally positioned for an infant's length and relatively immobilized.

Referring again to FIGS. 4 and 5, a three-point restraint harness 102 with a leg strap 100 and two shoulder straps 104 is affixed to the mattress 60. The non-buckling end of the leg strap 100 is stitched into the top surface 64 of the mattress 60 adjacent to the end of the mattress 60 opposite the headrest portion 106. Preferably the non-buckling end of each of the shoulder straps 104 is stitched to the rim 78 of the depression 70, although it is anticipated that the shoulder straps 104 could be secured to the ridge 74, the intermediate surface 76, or the top surface 64 of the headrest portion 106 instead. It is also contemplated that other means of securing the harness 102 to the mattress 60, such as fastening or adhesively securing the harness 102 to the top surface 64, may be used. Alternatively the leg strap 100 and shoulder straps 104 may be disposed through the mattress and secured to the bottom surface 62 using hook-and-loop materials or other securing means. Similarly, a single shoulder strap 104 could be looped through securing slots (not shown) disposed through the headrest portion 106 of the mattress 60, as described with reference to FIG. 12. Moreover, other alternative embodiments of the mattress 60 contemplate the use of other restraint harnesses, such as a five-point restraint harness.

Figure 8:
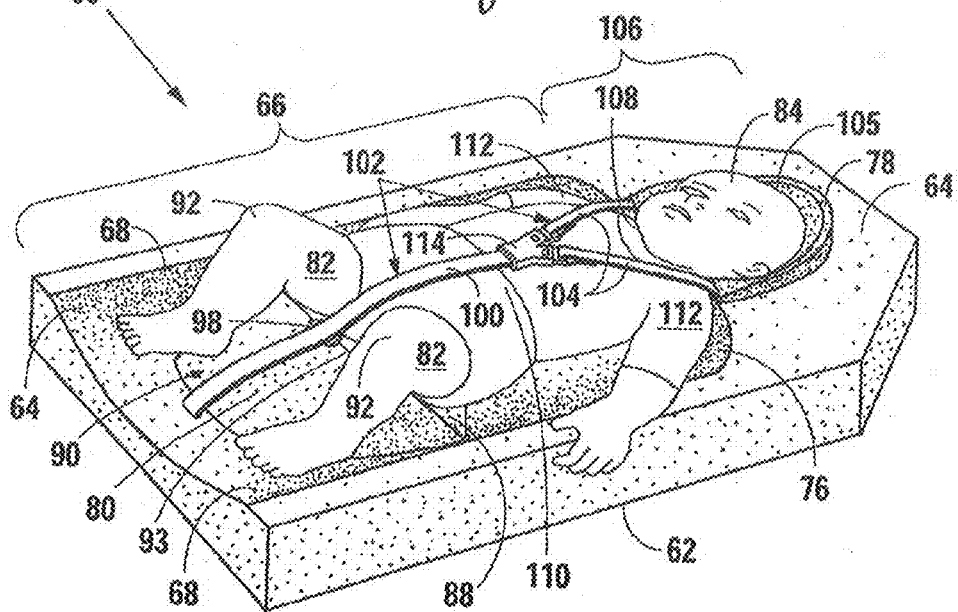
FIG. 8 is a perspective view of an infant positioned in the alternative embodiment of FIG. 4.

FIG. 8 is a perspective view of the first alternative embodiment of the present invention in normal operation with an infant 84 positioned on the mattress 60. For correction of an abnormally shaped infant cranium 105, the mattress 60 is placed on a resting surface (not shown) so that the bottom surface 62 is in contact therewith. Prior to placing the infant 84 on the mattress 60, the leg rest 80 is moved to a position accommodating the size of the infant 84 such that when the infant's cranium 105 is placed in the depression 70, the infant's knees 92 will be located over the apex 93 of the leg rest 80. In this position, the portion of the infant's legs 82 above the knees 92 is supported by the first side 88 of the leg rest 80, and the portion of the infant's legs 82 below the knees 92 is supported by the second side 90 of the leg rest 80.

The infant 84 is then placed in the mattress 60 in a supine position where the infant's cranium 105 rests in the depression 70. When in this position, the infant's neck 108 rests on the ridge 74, which provides support for the infant's neck 108 and makes sleeping and resting more comfortable. The infant's body 110 rests on the concave body portion 66 of the mattress 60. Should the infant 84 try to roll or move from a supine the position, the raised sides 68 of the top surface 64 impede the rolling or moving action, thus helping to prevent the infant 84 from inadvertently repositioning to a sideways or prone position on the mattress 60. Initially the posterior and part of the side aspects of the infant's cranium 105 contact the semi-rigid surface 72 of the depression 70, although during the sleep period the infant's cranium 105 may roll to one side or the other. In addition, the leg rest 80 aids in immobilizing the infant 84 while providing greater comfort by allowing a bend in the infant's legs 82. The infant's shoulders 112 are aligned in and cradled by the curved intermediate surface 76. The leg strap 100 and shoulder straps 104 of the restraint harness 102 are thereafter fastened at the buckle 114. The leg strap 100 is placed across the leg strap guide 98 at the apex 93 of the leg rest 80, which helps to prohibit agitating contact between the leg strap 100 and the infant 84. After fastening the leg strap 100 to the shoulder straps 104, the harness 102 is adjustable to the size of the infant's body 110, and the shoulder straps 104 and leg strap 100 may be tightened to fit snugly but comfortably thereabout.

As the infant's cranium 105 makes contact with the semi-rigid surface 72, the semi-rigid surface 72 provides external forces acting on any abnormal bulges of the infant's cranium 105 and diminishes or eliminates external forces that act on abnormal depressions of the infant's cranium 105. This contact reduces the net outward forces from brain and skull growth at the bulges, and redirects the growth to areas of depression in the cranium that are lightly touching or not in contact with the semi-rigid surface 72.

The mattress 60 works similarly to prevent cranial deformities. With the infant's cranium 105 placed in the depression 70, the semi-rigid surface 72 of the depression 70 matches the round, normally-shaped contour of the posterior and side aspects of the infant's cranium 105. Thus, the semi-rigid surface 72 substantially and continuously contacts the entire surface area of the cranium 105 within the depression 70. Forces from the semi-rigid surface 72 act on the area of the cranium 105 in contact with the semi-rigid surface 72. The resulting pressure causes the infant's cranium 105 to grow evenly and maintain its normal shape. In other words, the contour of the normally-shaped semi-rigid surface 72 allows for the development of normal cranial shaping regardless of the cranium's 105 resting position by preventing abnormal growth (i.e., cranial bulges and cranial depressions) in the area of contact with the semi-rigid surface 72. The pressure caused by the forces acting on the cranium from the semi-rigid surface 72 is preferably substantially isometric.

Figure 9:
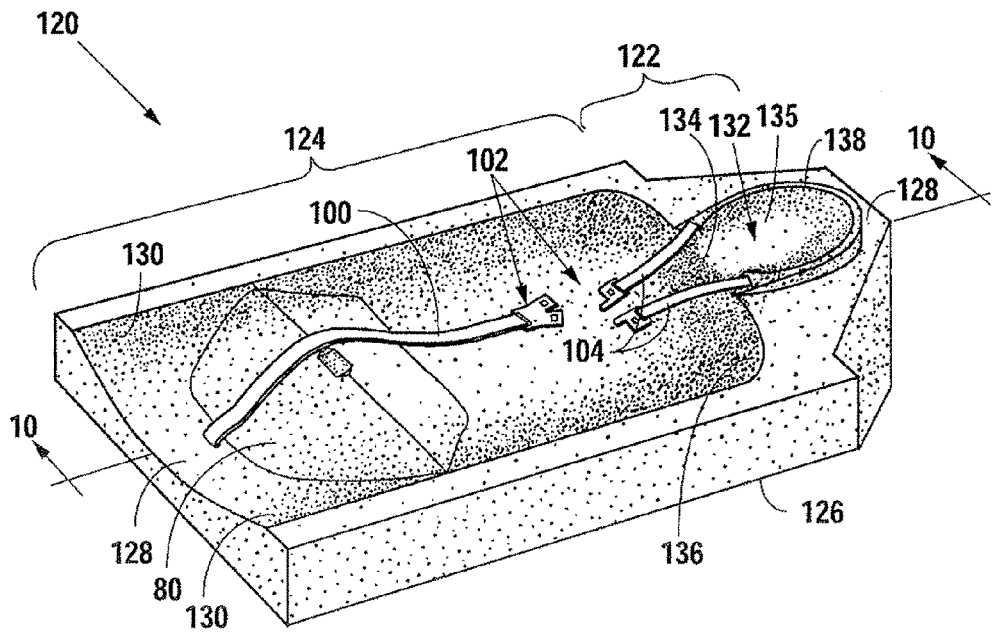
FIG. 9 shows a perspective view of a second alternative embodiment of the mattress wherein a headrest portion of the top surface is inclined relative to a body portion of the mattress.
Figure 10:
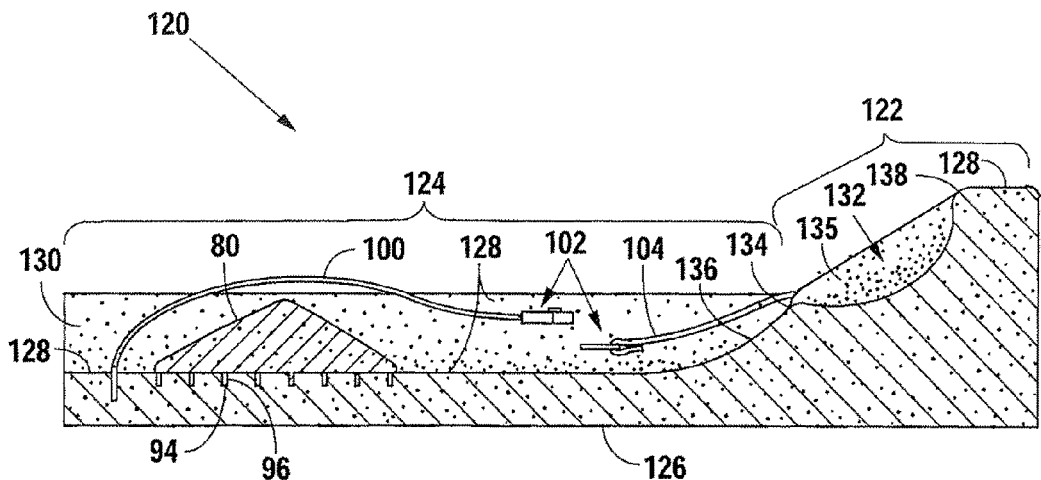
FIG. 10 is a sectional view of the second alternative embodiment along section line 10-10 of FIG. 9.

FIG. 9 and FIG. 10 (in combination with FIG. 6A & FIG. 6B) depict a second alternative embodiment of the present invention. FIG. 9 shows this embodiment of the mattress 120 wherein a headrest portion 122 of the mattress 120 is angled relative to a body portion 124 of the mattress 120.

As shown in FIGS. 9 and 10, the mattress 120 comprises a bottom surface 126 and a top surface 128. A body portion 124 of the top surface 128 of the mattress 120 is concave and has raised sides 130 to prevent an infant (not shown) lying on the mattress 120 from rolling or moving from the infant's resting or sleeping position. The top surface 128 of the headrest portion 122 of the mattress 120 is inclined relative to the body portion 124 of the mattress 120. The headrest portion 122 of the mattress 120 further comprises a generally hemi-ellipsoidal depression 132 in the top surface 128 of the headrest portion 122. The depression 132 corresponds to the shape of a normal infantile cranium. A semi-rigid surface 135 of the depression 132 is resilient, and preferably made of self-skinning foam. A ridge 134 is adjacent to one end of the depression 132, and a curved intermediate surface 136 is positioned between the ridge 134 and the concave body portion 124 of the top surface 128. A rim 138 defines a substantial portion of the depression 132.

This alternative embodiment includes a leg rest 80 for positioning an infant's legs thereon to increase the infant's comfort and to more effectively immobilize the infant during use, as is described with reference to FIGS. 6A and 6B. This alternative embodiment also contemplates a three-point restraint harness 102 with a leg strap 100 and two shoulder straps 104 affixed to the mattress 120, as has been previously described with reference to the first alternative embodiment. Moreover, other alternative embodiments of the invention contemplate the use of other restraint harnesses, such as a five-point restraint harness. Use of the harness 102 is as described with reference to FIG. 4 through FIG. 8.

The mattress 120 is preferably a single body molded from a self-skinning foam material. The mattress 120, however, may alternatively be made from a number of other materials, including closed cell foam layered over higher density foam or layered over a more rigid solid or hollow plastic. In addition, the mattress 120 may be made from open cell foam to which has been applied a surface treatment such as, for example, a vinyl or other coating, impregnating paint into the surface during the molding process, or painting the surface.

The embodiment disclosed by FIG. 9 and FIG. 10 is used in the same manner as the previously-described embodiments to correct and prevent abnormal cranial bulges and depressions in an infant's cranium. Because the headrest portion 122 of this is embodiment is angled relative to the body portion 124 of the mattress, the infant's head will be supported at an angle relative to the infant's body. In combination with the support provided to the infant's neck from the ridge 134 and to the infant's shoulders from the curved intermediate surface 136, this embodiment may provide a more comfortable resting position by elevating the infant's head.

Figure 13:
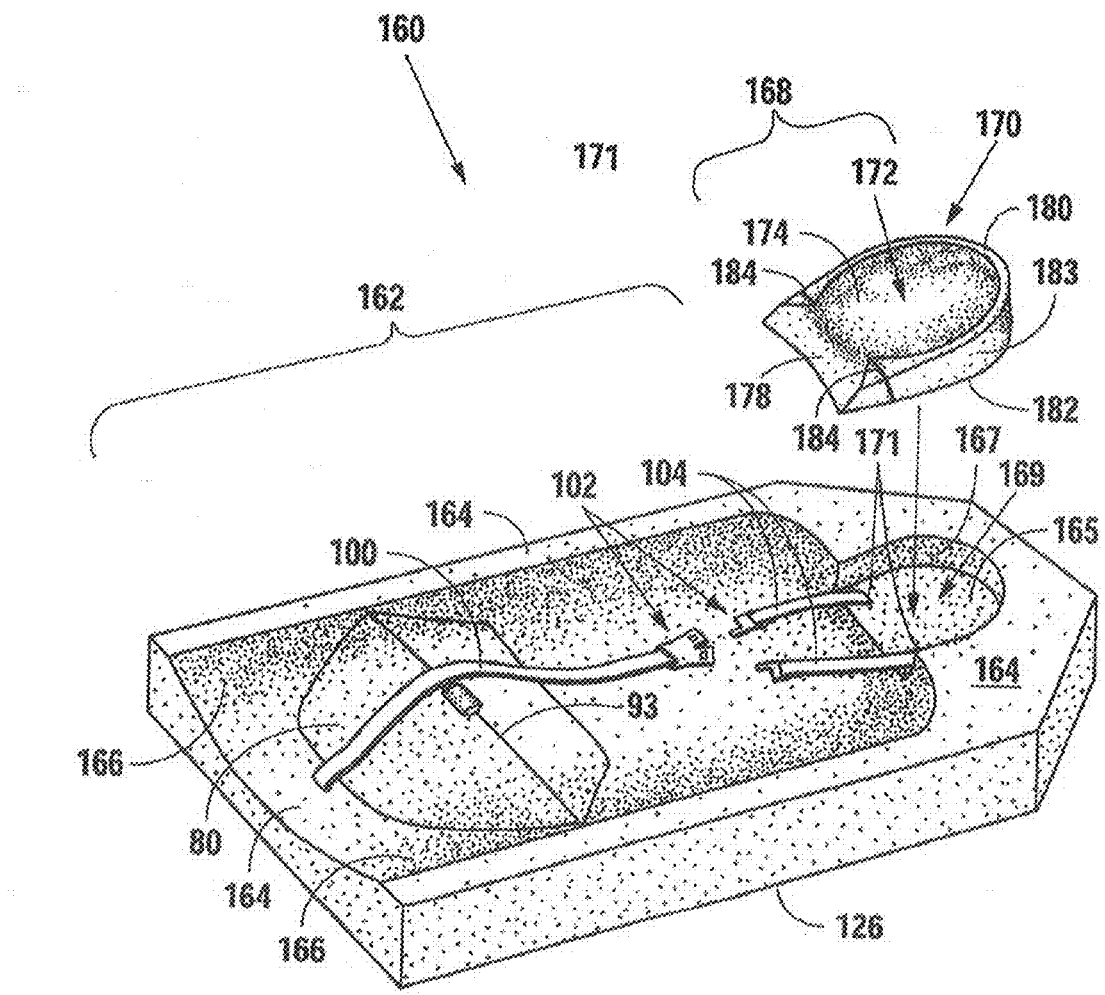
FIG. 13 shows a partially exploded view of the third alternative embodiment.

FIGS. 11 through 14 depict a third alternative embodiment of the present invention that incorporates a removable headrest 170. As shown in FIGS. 11 through 13, and as shown in the embodiments previously described, a mattress 160 has a top surface 164 having a body portion 162 that is concave and has raised sides 166 to prevent an infant lying on the mattress 160 from rolling or moving from the infant's sleeping or resting position. A leg rest 80 as has been previously described and shown in FIGS. 6A and 6B is placed on the top surface 164 for positioning an infant's legs thereon to increase the infant's comfort and to more effectively immobilize the infant during use. A three-point restraint harness 102 with a leg strap 100 and two shoulder straps 104 (or a five-point restraint harness) is also affixed to the mattress 160, as has been previously described with reference to FIG. 4 through FIG. 10. The headrest portion 168 of the top surface 164 of the mattress 160 includes a cavity 169 that is positioned, shaped, and sized to receive the removable headrest 170.

FIG. 13 illustrates an exploded view of the embodiment shown in FIGS. 11 and 12. The cavity 169 is positioned, shaped, and sized to receive the removable headrest 170 such that a sidewall 167 of the cavity 169 contacts a side surface 183 of the headrest 170 so that the headrest 170 fits snugly in the cavity 169. The two shoulder straps 104 of the restraint harness 102 extend through strap holes 171 disposed through the headrest portion 168 of the mattress 160 to the bottom surface 126. An opening of each of the strap holes 171 is positioned in the cavity surface 165 such that it will align with one of the strap slots 184 in the removable headrest 170 when the headrest 170 is placed into the cavity 169 (see FIG. 12). The ends of the shoulder straps 104 are secured to the bottom surface 126 using a hook-and-loop material, although it is anticipated that other means of securing the shoulder straps 104 to the bottom surface 126, such as adhesively securing or stitching, may be used. The shoulder straps 104 may thereafter be positioned in the strap slots 184 of the removable headrest 170 as the headrest 170 is received by the cavity 169.

Alternatively, instead of two shoulder straps 104 as shown in FIGS. 11 through 13, a single strap 104 may be used by threading the strap 104 downwardly through one strap hole 171 to the bottom surface 126, across the bottom surface 126 of the mattress 160, upwardly through another strap hole 171, and outwardly from the cavity surface 165. Thus, a single strap 104 may be looped through the headrest portion 168 of the mattress 160. As shown in FIG. 11, prior to placing the infant on the mattress 160, the removable headrest 170 is inserted into the cavity 169, which includes positioning the shoulder straps 104 through strap slots 184 in the headrest 170. The headrest's bottom surface 182 contacts the cavity surface 165, while the headrest's side surface 183 contacts the sidewall 167 of the cavity 169 to aid in immobilizing the headrest 170 relative to the headrest portion 168 of the mattress 160. In alternative embodiments, the headrest 170 may additionally be secured to the cavity surface 165 using a hook-and-loop material or other fastening means. Also prior to placing the infant on the mattress 160, the leg rest 80 is moved to a position accommodating the size of the infant such that when the infant's cranium is placed in the depression 172, the infant's knees will be located over the apex 93 of the leg rest 80. The restraint harness 102 is secured about the infant as described hereinabove with reference to the other disclosed embodiments. Thereafter, the infant is placed in the mattress 160 in a supine position where the infant's cranium rests in the depression 172.

Figure 14:
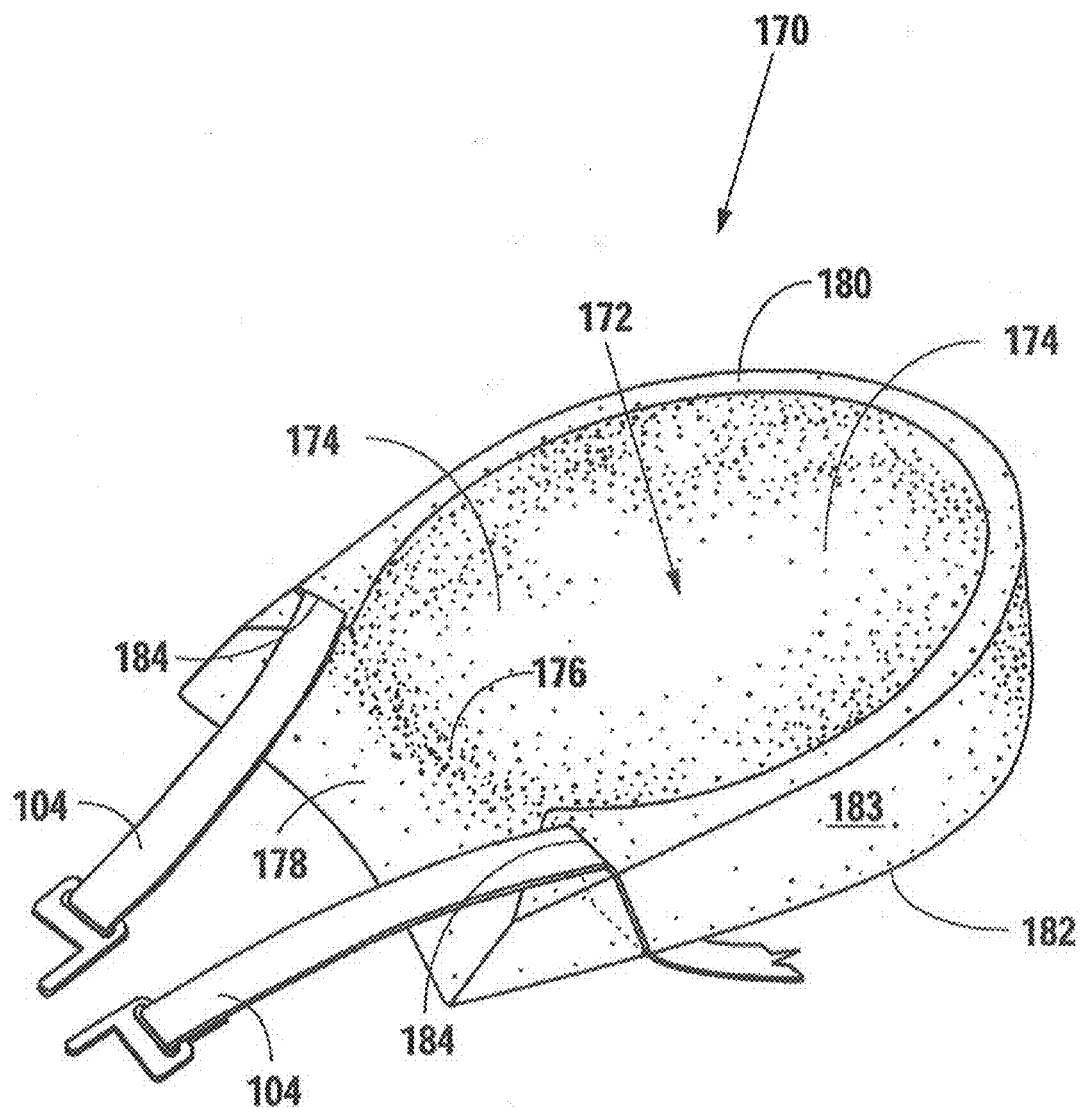
FIG. 14 depicts a perspective view of the removable headrest of the third embodiment in greater detail.

FIG. 14 depicts the removable headrest 170 in greater detail. The removable headrest 170 includes the bottom surface 182, the side surface 183, and a semi-rigid top surface 174 having a generally hemi-ellipsoidal depression 172 that corresponds to the shape of a normal infantile cranium. An outer rim 180 defines a substantial portion of the depression 172. The two strap slots 184 are disposed in the rim 180 and extend through the headrest 170 to its bottom surface 182. While the removable headrest 170 is itself preferably self-skinning foam, it may alternatively be made from a number of foam variants or other materials, including closed cell foam layered over higher density foam or layered over a more rigid solid or hollow plastic. In addition, the removable headrest 170 may be made from open cell foam to which has been applied a surface treatment such as a vinyl or other coating, impregnating paint into the surface during the molding process, or painting the surface. Use of this third alternative embodiment to correct and/or prevent cranial deformities in infants is thereafter the same as described with reference to the other embodiments.

The present invention is described above in terms of a preferred illustrative embodiment of a specifically described mattress incorporating a headrest, as well as alternative embodiments of the present invention. Those skilled in the art will recognize that alternative constructions of such a mattress can be used in carrying out the present invention. For example, although some of the embodiments described herein include a leg rest, other embodiments may not include a leg rest. Similarly, although some of the embodiments described herein include a three-point restraint harness, other embodiments may omit such a harness or include an alternative type of harness (e.g., a five-point restraint harness). Accordingly, other aspects, features, and advantages of the present invention may be obtained from a study of this disclosure and the drawings, along with the appended claims.

I claim:

1. A mattress for supporting a sleeping or resting infant and for correcting the shape of an infant's abnormally-shaped cranium comprising:
   a bottom surface;
   a top surface wherein at least a portion of said top surface has raised sides to prevent said infant from rolling or moving from a sleeping or resting position;
   a generally hemi-ellipsoidal depression in said top surface, said depression corresponding to the shape of a normal infantile cranium,
   said depression having a semi-rigid surface which demonstrates minimal focal elasticity only at the site of cutaneous contact
   said semi-rigid surface of said depression providing external forces acting on abnormal cranial bulges of said infant's cranium; and
   said semi-rigid surface of said depression minimizing external forces acting on abnormal cranial depressions of said infant's cranium.

2. The mattress of claim 1 wherein said portion of said top surface is concave.

3. The mattress of claim 1 wherein said external forces acting on abnormal cranial depressions are eliminated.

4. The mattress of claim 1 further comprising a leg rest for supporting legs of said infant while said infant is on said mattress, wherein the position of said leg rest is adjustable relative to said top surface of said mattress.

5. The mattress of claim 4 further comprising:
   at least one positioning slot in said top surface; and
   a positioning tab protruding from said leg rest for insertion into one of said at least one positioning slots.

6. The mattress of claim 4 or claim 5 wherein said leg rest further comprising:
   a leg rest bottom surface conforming to the shape of said top surface of said mattress; and
   a leg rest top surface having a first side for supporting the legs above said infant's knees, a second side for supporting said legs below said knees, said first and second sides joining at an apex for supporting said knees.

7. The mattress of claim 1 further comprising a ridge adjacent to said depression for supporting the neck of said infant.

8. The mattress of claim 7 further comprising a curved surface adjacent to said ridge for cradling the shoulders of said infant.

9. The mattress of claim 1 wherein said semi-rigid surface of said depression is resilient.

10. The mattress of claim 1 wherein said semi-rigid surface of said depression is self-skinning foam material.

11. The mattress of claim 1 wherein said semi-rigid surface of said depression is open cell foam material with a surface treatment.

12. The mattress of claim 1 further comprising a rim defining a substantial portion of said depression.

13. The mattress of claim 1 further comprising a restraint harness attached to said mattress to restrain said infant in a supine position while said infant's cranium is contacting said top surface.

14. A mattress for supporting a sleeping or resting infant and for preventing abnormal shaping of an infant's normally-shaped cranium comprising:
   a bottom surface;
   a top surface wherein at least a portion of said top surface has raised sides for preventing said infant from rolling or moving from a sleeping or resting position; and
   a generally hemi-ellipsoidal depression in said top surface, said depression corresponding to the shape of a normal infantile cranium, said depression having a semi-rigid surface for contacting and applying pressure to said infant's normally-shaped cranium to prevent development of abnormal cranial bulges and abnormal cranial depressions.

15. The mattress of claim 14 wherein said portion of said top surface is concave.

16. The mattress of claim 14 further comprising a leg rest for supporting legs of said infant while said infant is on said mattress, wherein the position of said leg rest is adjustable relative to said top surface of said mattress.

17. The mattress of claim 16 further comprising:
   at least one positioning slot in said top surface; and
   a positioning tab protruding from said leg rest for insertion into one of said at least one positioning slots.

18. The mattress of claim 16 or claim 17 wherein said leg rest further comprising:
   a bottom surface conforming to the shape of said top surface of said mattress; and
   a top surface having a first side for supporting the legs above said infant's knees, a second side for supporting said legs below said knees, said first and second sides joining at an apex for supporting said knees.

19. The mattress of claim 14 further comprising a ridge adjacent to said depression for supporting the neck of said infant.

20. The mattress of claim 19 further comprising a curved surface adjacent to said ridge for cradling the shoulders of said infant.

21. The mattress of claim 14 wherein said pressure is substantially isometric.

22. The mattress of claim 14 wherein said semi-rigid surface of said depression is resilient.

23. The mattress of claim 14 wherein said semi-rigid surface of said depression is self-skinning foam material.

24. The mattress of claim 14 wherein said semi-rigid surface of said depression is open cell foam material with a surface treatment.

25. The mattress of claim 14 further comprising a rim defining a substantial portion of said depression.

26. The mattress of claim 14 further comprising a restraint harness attached to said mattress to restrain said infant in a supine position while said infant's cranium is contacting said top surface.

27. A mattress for supporting a sleeping or resting infant and for correcting the shape of an infant's abnormally-shaped cranium comprising:
   a bottom surface;
   a top surface wherein at least a portion of said top surface has raised sides for preventing the infant from rolling or moving from a sleeping or resting position;
   a headrest integral with said top surface, said headrest having a generally hemi-ellipsoidal depression that corresponds to the shape of a normal infantile cranium, said depression having a semi-rigid surface for providing external forces acting on abnormal cranial bulges of said infant's cranium; and
   said semi-rigid surface of said depression minimizing external forces acting on abnormal cranial depressions of said infant's cranium.

28. The mattress of claim 27 wherein said portion of said top surface is concave.

29. The mattress of claim 27 wherein said external forces acting on abnormal cranial depressions are eliminated.

30. The mattress of claim 27 further comprising a rim defining a substantial portion of said depression.

31. The mattress of claim 27 further comprising a leg rest for supporting legs of said infant while said infant is on said mattress, wherein the position of said leg rest is adjustable relative to said top surface of said mattress.

32. The mattress of claim 31 further comprising:
at least one positioning slot in said top surface; and
a positioning tab protruding from said leg rest for insertion into one of said at least one positioning slots.

33. The mattress of claim 31 or claim 32 wherein said leg rest further comprising:
a leg rest bottom surface conforming to the shape of said top surface of said mattress; and
a leg rest top surface having a first side for supporting the legs above said infant's knees, a second side for supporting said legs below said knees, said first and second sides joining at an apex for supporting said knees.

34. The mattress of claim 31 further comprising a ridge adjacent to said depression for supporting the neck of said infant.

35. The mattress of claim 34 further comprising a curved surface adjacent to said ridge for cradling the shoulders of said infant.

36. The mattress of claim 27 wherein said semi-rigid surface of said depression is resilient.

37. The mattress of claim 27 wherein said semi-rigid surface of said depression is self-skinning foam material.

38. The mattress of claim 27 wherein said semi-rigid surface of said depression is open cell foam material with a surface treatment.

39. The mattress of claim 27 further comprising a restraint harness to restrain said infant in a supine position.

40. A mattress for supporting a sleeping or resting infant and for preventing abnormal shaping of an infant's normally shaped cranium comprising:
a bottom surface;
a top surface wherein at least a portion of said top surface has raised sides for preventing the infant from rolling or moving from a sleeping or resting position;
a headrest integral with said top surface, said headrest having a generally hemi-ellipsoidal depression that corresponds to the shape of a normal infantile cranium,
said depression having a semi-rigid surface which demonstrates minimal focal elasticity at the point of cutaneous contact for contacting and applying pressure to said infant's normally-shaped cranium to prevent development of abnormal cranial bulges and abnormal cranial depressions.

41. The mattress of claim 40 wherein said portion of said top surface is concave.

42. The mattress of claim 40 further comprising a rim defining a substantial portion of said depression.

43. The mattress of claim 40 further comprising a leg rest for supporting legs of said infant while said infant is on said mattress, wherein the position of said leg rest is adjustable relative to said top surface of said mattress.

44. The mattress of claim 43 further comprising:
at least one positioning slot in said top surface; and
a positioning tab protruding from said leg rest for insertion into one of said at least one positioning slots.

45. The mattress of claim 43 or claim 44 wherein said leg rest further comprising:
a leg rest bottom surface conforming to the shape of said top surface of said mattress; and
a leg rest top surface having a first side for supporting the legs above said infant's knees, a second side for supporting said legs below said knees, said first and second sides joining at an apex for supporting said knees.

46. The mattress of claim 40 further comprising a ridge adjacent to said depression for supporting the neck of said infant.

47. The mattress of claim 46 further comprising a curved surface adjacent to said ridge for cradling the shoulders of said infant.

48. The mattress of claim 40 wherein said pressure is substantially isometric.

49. The mattress of claim 40 wherein said semi-rigid surface of said depression is resilient.

50. The mattress of claim 40 wherein said semi-rigid surface of said depression is self-skinning foam material.

51. The mattress of claim 40 wherein said semi-rigid surface of said depression is open cell foam material with a surface treatment.

52. The mattress of claim 40 further comprising a restraint harness to restrain said infant in a supine position.

\* \* \* \* \*